US011912966B2

(12) United States Patent
Bashan et al.

(10) Patent No.: US 11,912,966 B2
(45) Date of Patent: Feb. 27, 2024

(54) SYSTEM AND METHOD FOR GROWING ALGAE

(71) Applicant: Vaxa Technologies Ltd, Rosh Pinna (IL)

(72) Inventors: Oded Bashan, Rosh Pina (IL); Ohad Bashan, Sde Varburg (IL); Stephen Drummey, North Easton, MA (US)

(73) Assignee: VAXA TECHNOLOGIES LTD, Rosh Pinna (IL)

( * ) Notice: Subject to any disclaimer, the term of this patent is extended or adjusted under 35 U.S.C. 154(b) by 894 days.

(21) Appl. No.: 16/518,440

(22) Filed: Jul. 22, 2019

(65) Prior Publication Data

US 2019/0345427 A1 Nov. 14, 2019

Related U.S. Application Data

(63) Continuation-in-part of application No. PCT/IL2018/050065, filed on Jan. 18, 2018, and a
(Continued)

(51) Int. Cl.
*C12M 1/00* (2006.01)
*C12N 1/12* (2006.01)
(Continued)

(52) U.S. Cl.
CPC ........... *C12M 21/02* (2013.01); *B01F 23/231* (2022.01); *C12M 29/06* (2013.01); *C12M 31/10* (2013.01);
(Continued)

(58) Field of Classification Search
None
See application file for complete search history.

(56) References Cited

U.S. PATENT DOCUMENTS

| 10,336,795 B2 | 7/2019 | Brain et al. |
| 2008/0068920 A1* | 3/2008 | Galliher ............... B01F 23/231 239/66 |

(Continued)

FOREIGN PATENT DOCUMENTS

| CN | 102826712 | 12/2012 |
| CN | 103649551 | 3/2014 |

(Continued)

OTHER PUBLICATIONS

Matthew R Melnicki et al., "Feedback-controlled LED photobioreactor for photophysiological studies of cyanobacteria", Bioresource Technology, vol. 134, Apr. 2013, pp. 127-133.
(Continued)

*Primary Examiner* — William H. Beisner
(74) *Attorney, Agent, or Firm* — PEARL COHEN ZEDEK LATZER BARATZ LLP

(57) ABSTRACT

Aspects of the invention are directed to a system and method of sparging an algae cultivation container. The method may include controlling at least one first sparger to distribute a first fluid into the container at a first operating flow rate; and controlling at least one second sparger to distribute a second fluid into the container at a second operating flow rate. The first operating flow rate may be adapted to allow mixing the algae in the cultivation container, and the second operating flow rate may be adapted to allow assimilation of materials in a liquid in the cultivation container.

14 Claims, 4 Drawing Sheets

Related U.S. Application Data continuation-in-part of application No. PCT/IL2018/050067, filed on Jan. 18, 2018, and a continuation-in-part of application No. PCT/IL2018/050066, filed on Jan. 18, 2018.

(60) Provisional application No. 62/449,042, filed on Jan. 22, 2017, provisional application No. 62/449,043, filed on Jan. 22, 2017, provisional application No. 62/449,045, filed on Jan. 22, 2017.

(51) Int. Cl.
*C12M 1/107* (2006.01)
*B01F 23/231* (2022.01)

(52) U.S. Cl.
CPC ............... *C12N 1/12* (2013.01); *C12M 23/36* (2013.01); *C12M 41/06* (2013.01)

(56) References Cited

U.S. PATENT DOCUMENTS

| | | | | |
|---|---|---|---|---|
| 2008/0139865 | A1* | 6/2008 | Galliher | C12M 41/14 588/249 |
| 2009/0011492 | A1* | 1/2009 | Berzin | C12M 23/08 435/257.1 |
| 2009/0047722 | A1* | 2/2009 | Wilkerson | C12M 31/10 435/257.1 |
| 2010/0099151 | A1 | 4/2010 | Stroiazzo-Mougin et al. | |
| 2010/0255458 | A1 | 10/2010 | Kinkaid | |
| 2011/0104790 | A1 | 5/2011 | Kassebaum et al. | |
| 2011/0258920 | A1* | 10/2011 | Licamele | C12M 27/00 47/1.4 |
| 2012/0010779 | A1 | 1/2012 | Staufer et al. | |
| 2012/0107792 | A1 | 5/2012 | Babbitt et al. | |
| 2012/0313267 | A1 | 12/2012 | Pradel et al. | |
| 2013/0230904 | A1* | 9/2013 | Suryo | C12M 31/06 435/257.1 |
| 2015/0087049 | A1* | 3/2015 | Ehwald | C12M 29/04 435/292.1 |
| 2015/0210970 | A1 | 7/2015 | Hellingwerf et al. | |
| 2016/0289620 | A1 | 10/2016 | Mazur et al. | |
| 2017/0145361 | A1 | 5/2017 | Bergmann et al. | |

FOREIGN PATENT DOCUMENTS

| | | | | |
|---|---|---|---|---|
| DE | 102005012515 A1 * | 9/2006 | | C12M 21/02 |
| EP | 2520642 | 11/2012 | | |
| GB | 2469085 | 10/2010 | | |
| JP | H06225778 A * | 8/1994 | | |
| JP | H07-246086 | 9/1995 | | |
| JP | 2007-068419 | 3/2007 | | |
| JP | 2010-530757 | 9/2010 | | |
| JP | 2014-516550 | 7/2014 | | |
| SU | 1401041 | 6/1988 | | |
| WO | WO 2006/020177 | 2/2006 | | |
| WO | WO 2011/035166 | 3/2011 | | |

OTHER PUBLICATIONS

Search Report from European Application No. 18741125.1, dated Sep. 29, 2020.
Search Report from European Application No. 18741822.3, dated Oct. 16, 2020.
Office Action from Japanese Application No. 2019-559874, dated Dec. 21, 2021.
Notice of Allowance from Russian Application No. 2019126512, dated Oct. 15, 2021.
Office Action from Japanese Application No. 2019-559873, dated Nov. 30, 2021.
International Search Report of Application No. PCT/IL2018/050065 dated May 21, 2018.
International Search Report of Application No. PCT/IL2018/050067 dated May 16, 2018.
International Search Report of Application No. PCT/IL2018/050066 dated May 17, 2018.
Office Action for Japanese App. No. 2019559873, dated Jun. 7, 2022.
Office Action for India App. No. 201917033727, dated Jun. 21, 2022.
Office Action for Chinese App. No. 201880016813.6, dated Jul. 25, 2022.
Gaytan-Luna et al., Effect of Green and Red Light in Lipid Accumulation and Transcritional Profile of Genes Implicated in Lipid Biosynthesis in Chlamydomonas reinhardtii, Biotechnol Prog, 2016, vol. 32 No 6. pp. 1404-1411, Published online Oct. 28, 2016.
Elomraghy et al., Bio-jet Fuel from Microalgae: Reducing Water Energy Requirements for Algae Growth, International Journal of Engineering and Science, vol. 1 Issue 2, pp. 22-30, published Sep. 2012.
María Cuaresma Franco et al., Cultivation of microalgae in a high irradiance area, PhD Thesis, Wageningen University, Wageningen, The Netherlands, Jan. 1, 2011; ISBN: 978-90-8585-954-3.

* cited by examiner

SYSTEM AND METHOD FOR GROWING ALGAE

CROSS-REFERENCE TO RELATED APPLICATIONS

This application is a Continuation in Part of PCT Patent Application No. PCT/IL2018/050065, filed Jan. 18, 2018, which claims the benefit of U.S. Provisional Patent Application No. 62/449,042, filed Jan. 22, 2017 and a Continuation in Part of PCT Patent Application No. PCT/IL2018/050066, filed Jan. 18, 2018, which claims the benefit of U.S. Provisional Patent Application 62/449,045, filed Jan. 22, 2017 and a Continuation in Part of PCT Application No. PCT/IL2018/050067, filed Jan. 18, 2018, which claims the benefit of U.S. Provisional Application No. 62/449,043, filed Jan. 22, 2017, all of which are hereby incorporated by reference.

FIELD OF THE INVENTION

The present invention generally relates to algae growth. More particularly, the present invention relates to systems and methods for enhancing algae growth.

BACKGROUND OF THE INVENTION

In recent years, algae cultivation in artificial conditions with bio-reactors (e.g., with bubble columns) has become increasingly common, for instance in order to produce biomass. For optimal conditions and accelerated growth, the algae (or microalgae) are supplied with $CO_2$-enriched air bubbles and illumination (either artificial illumination, or from sunlight). About 50% of algal biomass is carbon, obtained by fixing $CO_2$ photosynthetically, where carbon dioxide needs to be dissolved into the culture in a liquid phase. In phototropic algae cultivation systems the major inputs (or macro-nutrients) for growth are light, $CO_2$, nutrients (such as Nitrogen, Phosphorus, etc.), and water with turbulent mixing in order to distribute those resources to individual algae cultivation cells.

Additionally, good fluid mixing is required for achieving high algae concentration in bio-reactors. Good mixing can manage the cell light exposure, by reducing the degree of mutual shading and minimizing photo-inhibition. Efficient mixing can move the cells close to the illuminated surface to obtain a photon input, and then away from it, in order to give the photon-saturated cells the opportunity to absorb this light energy for photosynthesis, before the cells are exposed to the light again. Since ultra-high cell concentrations require the usage of powerful light sources, inadequate mixing might result with over-exposure to high light, and also cell damage due to photo-inhibition.

Gas sparging (mainly air or Nitrogen enriched with $CO_2$) is commonly used in photo-bioreactors (PBRs) in order to create the required mixing. The rising motion of the bubbles creates mixing tangential to the flow direction. Efficient mixing usually requires continuous high flow rates and large bubbles. However, using sparging air flow for mixing and enriching its composition with $CO_2$ have inherent inefficiency since the $CO_2$ is introduced in large bubbles (required for mixing) in a diluted concentration, thus resulting with poor $CO_2$ biological usage of about 10% (with about 90% of the $CO_2$ emitted out of the bio-reactor).

Microalgae can be photographically grown in many types of systems, such as flat panel photo-bio-reactors. Light sources for algae growth can be any type of visible light in the range of about 400-700 nm wavelengths. Light emitting diodes (LEDs) have the capability of providing light of specific wavelengths, for example in the visible light (e.g., blue and/or red) wavelength range.

However, some inputs become limiting (e.g., limited light due to algae self-shading) and result in a determined maximal density of algae in a given system. If all other inputs are supplied at non-limiting availability, as algal culture increases in density, the cells shade the cells that are blocked in the path of the light. Eventually light fails to penetrate far enough into the culture to allow for more growth, and the system reached its maximal (light-limited) concentration.

SUMMARY OF THE INVENTION

Some aspects of the invention may be directed to a method of sparging an algae cultivation container. The method may include controlling at least one first sparger to distribute a first fluid into the container at a first operating flow rate; and controlling at least one second sparger to distribute a second fluid into the container at a second operating flow rate. In some embodiments, the first operating flow rate may be adapted to allow mixing the algae in the cultivation container, and the second operating flow rate may be adapted to allow assimilation of materials in a liquid in the cultivation container.

In some embodiments, the method may further include changing operating flow rate of the at least one second sparger according to changes in the at least one measured parameter. In some embodiments, the method may further include illuminating the container at a predetermined wavelength with at least one light source.

Some additional aspects of the invention may be directed to an algae cultivation container sparging system. The algae cultivation container sparging system may include at least one sensor, to measure at least one parameter within the container; at least one first sparger, to distribute a first fluid into the container at a first operating flow rate and at least one second sparger, to distribute a second fluid into the container at a second operating flow rate based on the at least one measured parameter. The algae cultivation container sparging system may further include at least one controller, to control the first operating flow rate and the second operating flow rate. In some embodiments the first operating flow rate may be adapted to allow turbulent mixing the algae in the cultivation container, and the second operating flow rate may be adapted to allow assimilation of materials in a liquid in the cultivation container.

In some embodiments, the at least one first sparger may have a diameter larger than 1 millimeter. In some embodiments, the at least one second sparger may have a diameter smaller than 1 millimeter. In some embodiments, the predetermined fluid may be selected from the group consisting of air and Nitrogen. In some embodiments, the algae cultivation container sparging system may further include a physical barrier to separate fluids distributed by first sparger and second sparger. In some embodiments, the at least one second sparger may be configured to distribute carbon-dioxide bubbles into the container. In some embodiments, the first operating flow rate of the at least one first sparger may be 100 millimeters/minute. In some embodiments, the first operating flow rate of the at least one second sparger may be 5 millimeters/minute.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
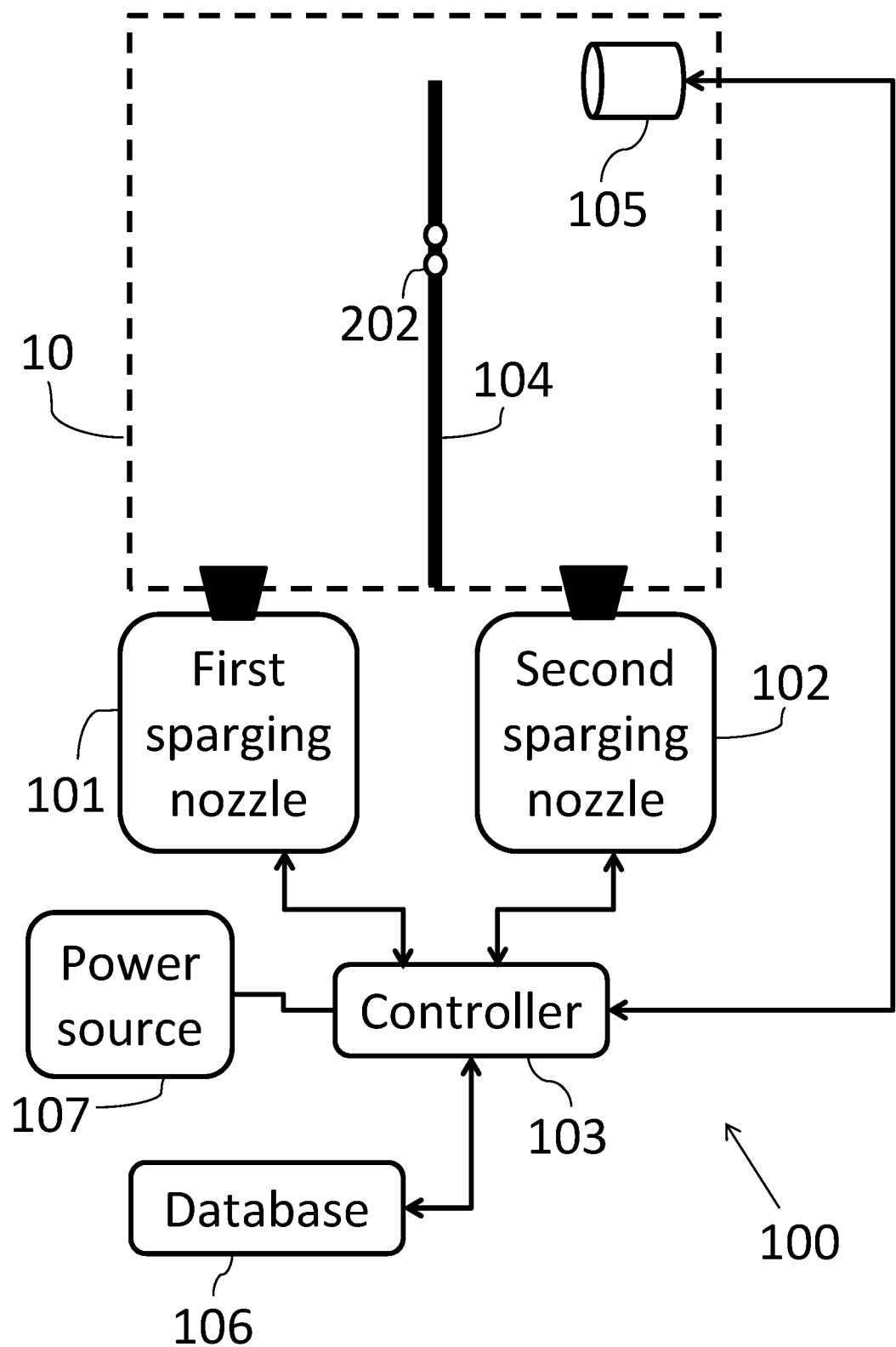
FIG. 1 schematically illustrates a block diagram of an algae cultivation container sparging system, according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Reference is now made to FIG. 1, which schematically illustrates a block diagram of an algae cultivation container sparging system 100, according to some embodiments of the invention. It should be noted that the direction of arrows in FIG. 1 may indicate the direction of information flow.

In some embodiments, sparging system 100 may include at least one first sparger 101 with a plurality of nozzles, to distribute a first predetermined fluid (e.g., air and/or Nitrogen bubbles) into a water filled algae cultivation container 10 (e.g., a bio-reactor) at a first operating flow rate so as to allow mixing therein. Sparging system 100 may further include at least one second sparger 102 with a plurality of nozzles, to distribute a second predetermined fluid (e.g., including gas bubbles with $CO_2$ and/or dissolved Phosphorus for mass transfer) into the container 10 at a second operating flow rate.

In some embodiments, sparging system 100 may include at least one controller 103, to control the first operating flow rate and the second operating flow rate. According to some embodiments, at least one nozzle of first sparger 101 and second sparger 102 may distribute fluid into cultivation container 10 based on a request from at least one controller 103, as further described hereinafter. In some embodiments, first operating flow rate may be based on the second operating flow rate. In some embodiments, at least one of the first operating flow rate and the second operating flow rate is predetermined.

In some embodiments, the first operating flow rate may be adapted to allow turbulent mixing of the algae in cultivation container 10. In some embodiments, the second operating flow rate may be adapted to allow mass transfer and/or assimilation of materials in a liquid in cultivation container 10.

In some embodiments, second predetermined fluid may include gas bubbles with over 30% $CO_2$ concentration. According to some embodiments, the source for at least one first predetermined fluid and second predetermined fluid may be external to sparging system 100, for example geothermal power stations may provide a source of dissolved Carbon and/or Sulfur for the second predetermined fluid.

In some embodiments, the first operating flow rate of at least one nozzle of first sparger 101 (e.g., 100 millimeters/minute) may be different from the second operating flow rate of at least one nozzle of second sparger 102 (e.g., 5 millimeters/minute).

In some embodiments, at least one nozzle of first sparger 101 may have a diameter larger than ~1 millimeter. In some embodiments, at least one nozzle of second sparger 102 may have a diameter smaller than ~1 millimeter. In some embodiments, nozzles of first sparger 101 as well as of second sparger 102 may distribute the same fluid (e.g., air), with nozzles of each sparger having different diameters.

In some embodiments, sparging system 100 may further include a physical barrier 104 to separate first fluid distributed by first sparger 101 and second fluid distributed by second sparger 102 within cultivation container 10. In some embodiments, at least one nozzle of first sparger 101 and/or second sparger 102 may be embedded into physical barrier 104. In some embodiments, physical barrier 104 may be adapted to allow flow from one side of the barrier (with first fluid distribution) to the other side (with second fluid distribution) at predefined (e.g., upper and lower) locations of the cultivation container 10, in order to create a controlled flow within the container 10.

In some embodiments, sparging system 100 may further include at least one sensor 105 (e.g., temperature sensor) coupled to controller 103 and configured to detect at least one feature within cultivation container 10. For example, at least one sensor 105 may detect at least one of pH levels, temperature and pressure conditions within cultivation container 10. In some embodiments, at least one sensor 105 may also detect parameters external to cultivation container 10, for example measuring mass flow of the gas emissions from cultivation container 10 to determine amount of substance that was absorbed in the algae cells by subtracting the emitted amount from the amount inserted into the container (e.g., by second sparger 102).

In some embodiments, sparging system 100 may further include at least one database 106 (or memory unit) configured to store algorithms for operation of controller 103, for instance database of operating rates for each nozzle and/or each sparger. In some embodiments, sparging system 100 may further include a power source 107 coupled to controller 103 and configured to provide electrical power to sparging system 100, whereby the power source 107 is adapted to power at least one first sparger 101 and at least one second sparger 102 to operate at different rates.

In some embodiments, data gathered by at least one sensor 105 may be analyzed by controller (or processor) 103 to detects if an attribute exceeds a predetermined threshold, for instance threshold for pH level and/or temperature and/or $CO_2$ concentration within the container 10. In case that conditions within cultivation container 10 (e.g., as detected by sensor 105) exceed at least one threshold, then controller 103 may operate at least one nozzle of first sparger 101 and/or at least one nozzle of second sparger 102 at a different flow rate. For example, detecting $CO_2$ concentration within the container 10 exceeds 40% (or detecting low pH levels) may cause at least one nozzle of second sparger 102 to lower flow rate of second sparger 102 to ~2 millimeters/minute. In some embodiments, at least one nozzle of second sparger 102 may operate only upon receiving a signal from sensor 105 that an attribute exceeds a predetermined threshold, and not operated in a constant rate.

In some embodiments, at least one nozzle of first sparger 101 may operate only upon receiving a signal from sensor 105 that an attribute exceeds a predetermined threshold, for example increasing mixing flow as the density of algal population increases. According to some embodiments, at least one nozzle of first sparger 101 and/or at least one nozzle of second sparger 102 may operate in a constant rate whereby the operation is not continuous. According to some embodiments, at least one nozzle of first sparger 101 and/or at least one nozzle of second sparger 102 may operate in a non-constant rate whereby the operation is also not continuous.

In some embodiments, cultivation container 10 may have a bubble column configuration with at least one first sparger 101 and at least one second sparger 102 positioned on the same surface of the bubble column container. In some embodiments, cultivation container 10 may have an airlift configuration with at least one second sparger 102 positioned at a bottom portion of a down-comer that may be distal to sensor 105, such that residence time of bubbles from the at least one second sparger 102 may be enhanced.

In some embodiments, sparging system 100 may allow at least 20% organic carbon within container 10, calculated over carbon provided as $CO_2$ bubbles. In some embodiments, at least a portion of the algae within container 10 is *Chlorella vulgaris*. In some embodiments, at least a portion of the algae within container 10 is Nannochloropsis. In some embodiments, at least a portion of the algae within container 10 is *Isochrysis* galban.

Figure 2A:
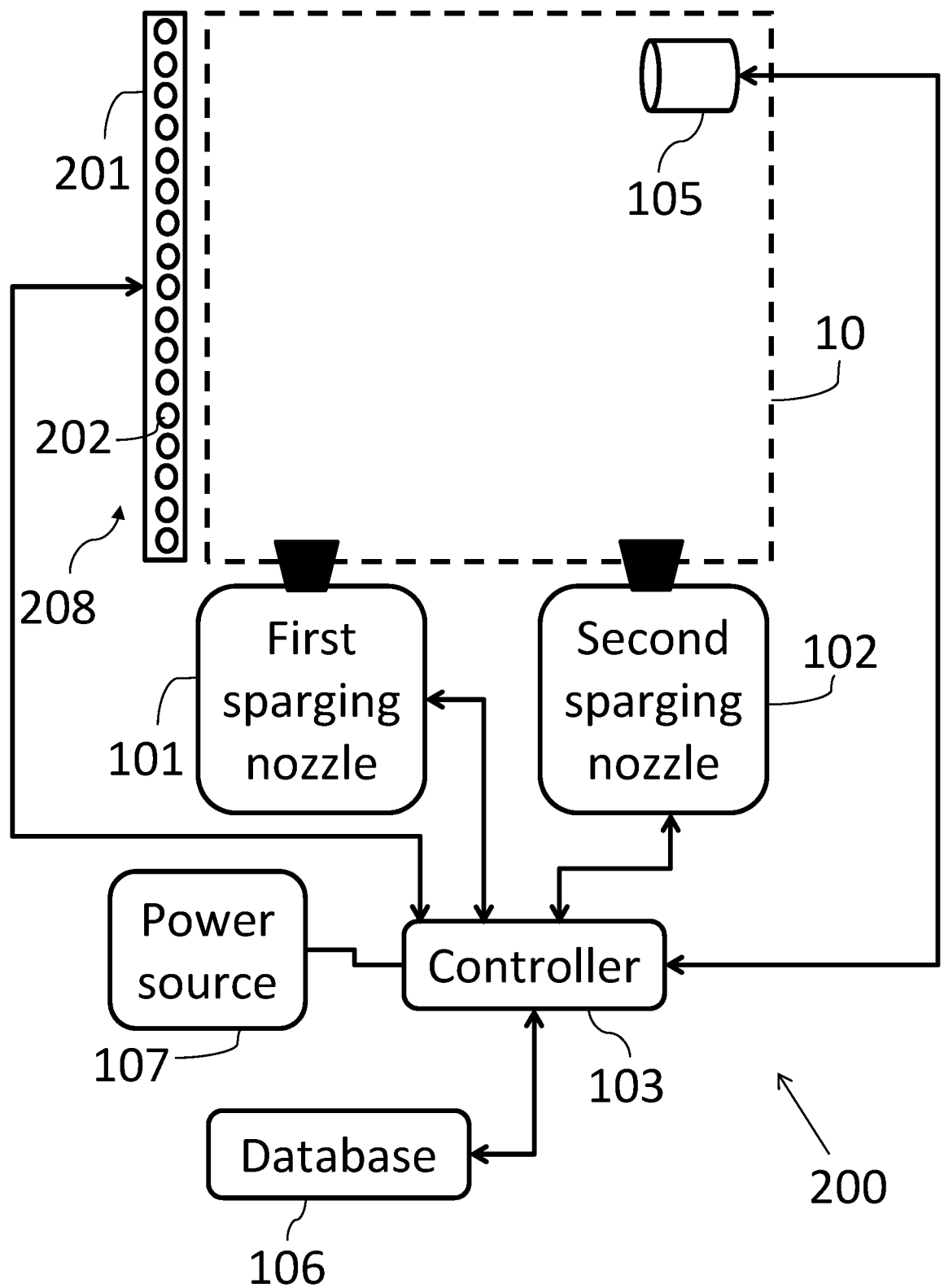
FIG. 2A schematically illustrates a block diagram of an algae cultivation container sparging system with at least one illumination unit, according to some embodiments of the invention.

Reference is now made to FIG. 2A, which schematically illustrates a block diagram of an algae cultivation container sparging system 200 with at least one illumination unit 201, according to some embodiments of the invention. It should be noted that the direction of arrows in FIG. 2A may indicate the direction of information flow.

In some embodiments, algae cultivation container sparging system 200 may include at least one illumination unit 201, coupled to controller 103, to illuminate cultivation container 10. In some embodiments, at least one illumination unit 201 and controller 103 (or another controller) may be included in a bioreactor illumination system 208 for algae growth. In some embodiments, the distance between cultivation container 10 and at least one illumination unit 201 may be modified so as to control the illumination received by cultivation container 10. For example, bringing at least one illumination unit 201 closer to cultivation container 10 so as to increase illumination of algae therein. In some embodiments, the distance between cultivation container 10 and at least one illumination unit 201 may be controlled by controller 103, for example, included in illumination system 208. According to some embodiments, in addition to, or instead of changing the distance of illumination unit 201 from cultivation container 10, the illumination intensity light sources 202 in illumination unit 201, may be controlled.

In some embodiments, at least one illumination unit 201 may include at least one light source 202 (e.g., LED) such that each light source 202 may be controlled separately by controller 103. In some embodiments, at least one light source 202 may be controlled to illuminate with a different intensity than another light source 202. According to some embodiments, all light sources 202 may be controlled to change the illumination intensity, either manually or according to preset timing and/or sensed conditions in cultivation container 10.

In some embodiments, cultivation container 10 with physical barrier 104 may include at least one light source 202 embedded into the physical barrier 104 (as shown in FIG. 1) such that container 10 may be illuminated from within, i.e. from at least one light source 202 embedded into the physical barrier 104. According to some embodiments, cultivation container 10 may include a plurality of physical barriers 104, each including at least one light source 202, such that a modular system may be created with algae growing between adjacent physical barriers 104, where at least one controller 103 may control illumination for all light sources 202 embedded into the physical barriers 104.

As may be apparent to one of ordinary skill in the art, the amount of light delivered to cultivation container 10 may be defined as an average of light flux delivered to the surface of the cultivation container 10. Thus, sparging system 200 for ultra-high density cultures (e.g., density above ~5 gram/liter) at least one illumination unit 201 may have light distribution of at least one light source 202 so as to provide average light flux substantially equal to average light flux of low density cultures (e.g., density below ~5 gram/liter) achieving similar light penetration, while at least one illumination unit 201 may have higher intensity for each light source 202. In some embodiments, light intensity within cultivation container 10 may be measured with at least one sensor 105.

For example, for ultra-high density cultures the light passage may be short (e.g., ~1-5 millimeters of illuminated zone with ~20-30 millimeters of dark zone) so that algae cells adjacent to the illumination unit 201 may be photo-inhibited (sub-lethal effect to algae) and/or photo-bleached (lethal effect to algae) so illumination unit 201 may be initially kept at a distance from container 10 to allow some growth of the algae, and then brought closer (e.g., once a day) so as to further increase the algae growth. In some embodiments, ultra-high density cultures may require mixing so as to allow illumination cycles for the algae (between the illuminated and dark zones) due to the short light passage. In some embodiments, ultra-high density cultures may be illuminated with various wavelengths since in such densities the wavelength may have nearly no effect on the growth due to the short light passage. It should be noted that according to common practice algae are illumination with specific wavelengths (e.g., with blue light) for normal growth since algae should respond to light differently, however experiments conducted by the applicants have shown that illumination with any wavelength may be used for ultra-high density cultures.

According to some embodiments, the light penetration into cultivation container 10 may correspond to at least one of the light intensity, the light wavelength, the specific algal strain, and/or the algal culture density. It should be noted that the light penetration into cultivation container 10 may determine the ration between illuminated zones and dark zones within the cultivation container 10, and thus may affect the light intensity provided by illumination units 201, the gas flow rate through first sparger 101, the gas flow rate through second sparger 102, etc.

In some embodiments, cultivation container 10 may be illuminated by at least one illumination unit 201 to provide a daily amount of over 90% of maximal algae growth within the cultivation container 10.

In some embodiments, at least one illumination unit 201 may include a configuration of low distribution of high intensity light sources 202. Such a configuration may allow enhanced algae growth compared with common practice configurations with homogenous distribution of low intensity light sources. In some embodiments, the illumination photon flux density of at least one light source 202 is 1200 micromole/meter$^2$/second. In some embodiments, at least one illumination unit 201 may include at least four light sources 202 for each square meter. For example, an illumination unit 201 having a surface area of about 6 meters a light path of about 4 cm may include 24 LED light sources 202, each having light flux of 1200 micromole/meter$^2$/second. In some embodiments, at least a portion of the algae within container 10 is *Isochrysis* galban.

In some embodiments, controller 103 may be configured to control the illumination wavelength of the at least one light source 202, for instance with a dedicated illumination module adapted to modify the wavelength of the emitted illumination. In some embodiments, a constant temperature of 27° C. may be maintained within the container 10.

In some embodiments, controller 103 may be configured to control at least one light source 202 to illuminate with wavelength of 650 nanometers. It should be noted that according to common practice algae are illumination with a particular wavelength (e.g., with blue light) for optimal growth, however experiments conducted by the applicants have shown that illumination with other wavelengths (e.g., with red light) may be used for enhanced growth.

Figure 2B:
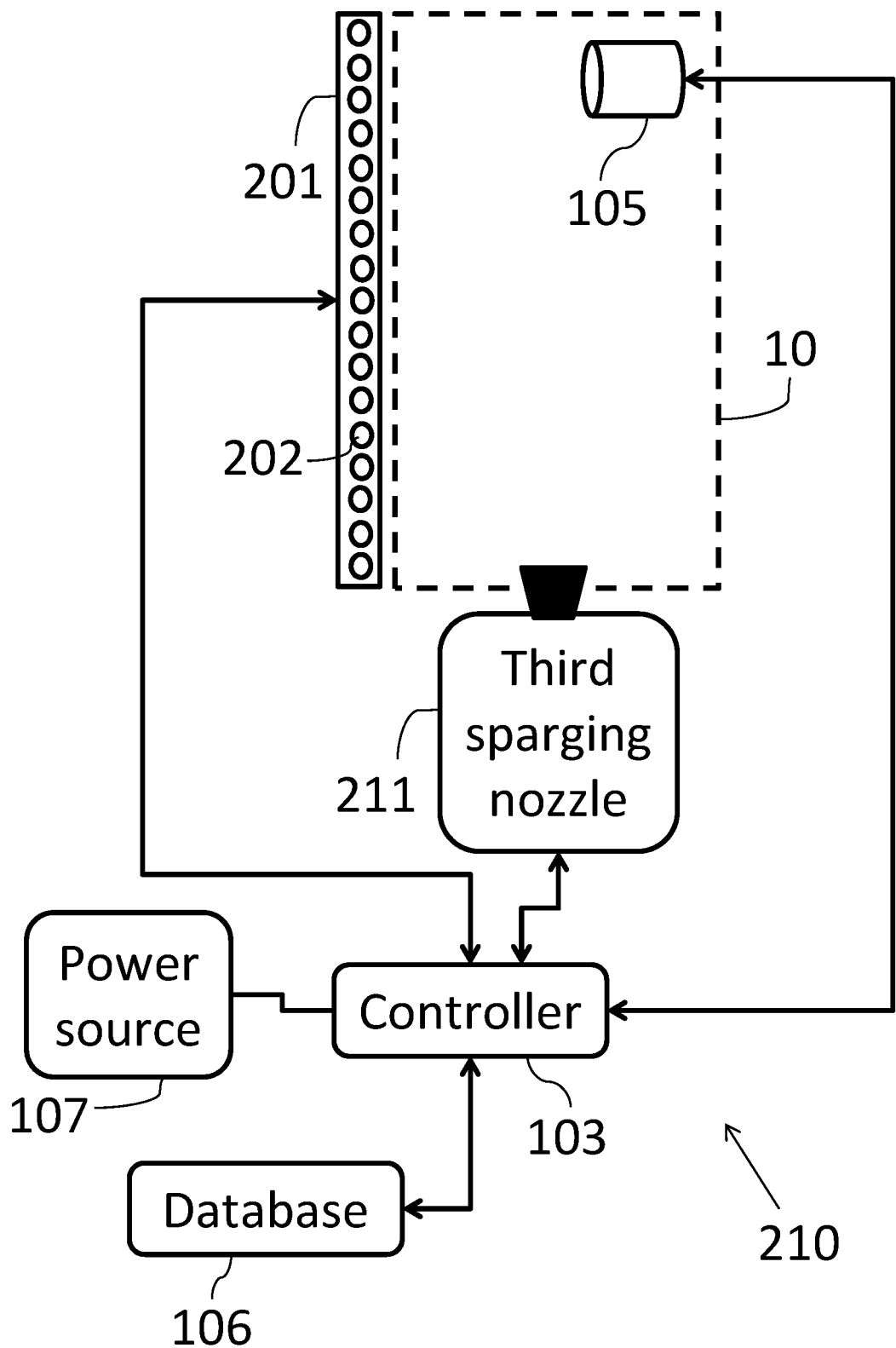
FIG. 2B schematically illustrates a block diagram of an algae cultivation container sparging system 200 with at least one illumination unit 201 and a single sparger, according to some embodiments of the invention.

Reference is now made to FIG. 2B, which schematically illustrates a block diagram of an algae cultivation container sparging system 210 with at least one illumination unit 201 and a single third sparger 211, according to some embodiments of the invention. It should be noted that the direction of arrows in FIG. 2B may indicate the direction of information flow.

In some embodiments, sparging system 210 may include at least one illumination unit 201 with at least one third sparger 211 (with at least one nozzle) that is configured to distribute a predetermined fluid into the cultivation container 10. In some embodiments, at least one third sparger 211 may include at least one nozzle to distribute a first predetermined fluid and at least one nozzle (e.g., having a different diameter) to distribute a second predetermined fluid. In some embodiments, at least one third sparger 211 may be adapted to allow turbulent mixing the algae in the cultivation container 10, as well as adapted to allow assimilation of $CO_2$ in a liquid in the container 10.

Figure 3:
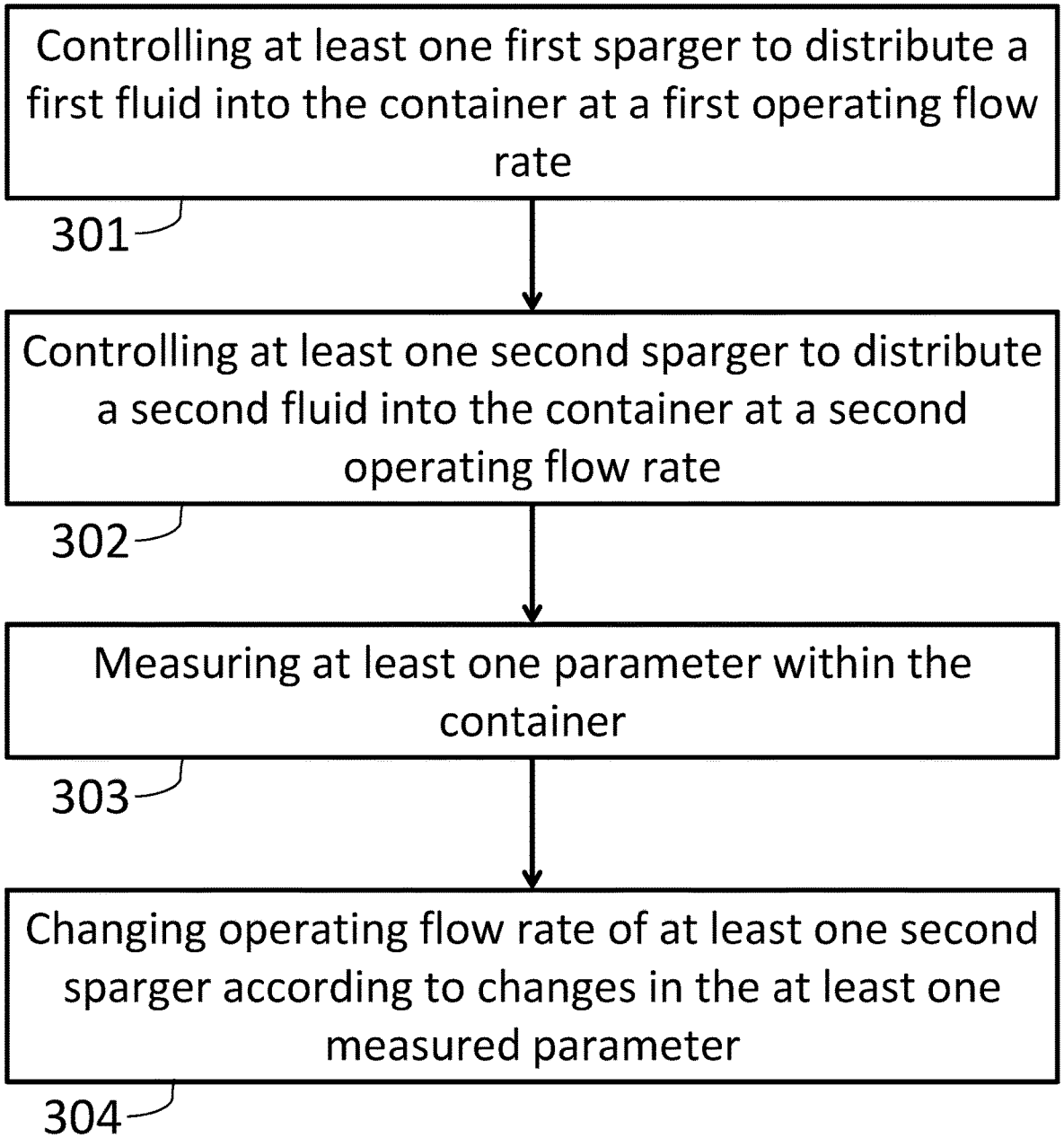
FIG. 3 shows a flow chart for a method of sparging an algae cultivation container, according to some embodiments of the invention.

Reference is now made to FIG. 3, which shows a flowchart of a method of sparging an algae cultivation container 10, according to some embodiments of the invention. In some embodiments, the method may include controlling 301 at least one first sparger 101 to distribute a first fluid into the container 10 at a first operating flow rate. In some embodiments, the method may further include controlling 302 second sparger 102 to distribute a second fluid into the container 10 at a second operating flow rate. In some embodiments, the first operating flow rate of at least one first sparger 101 may be different from the second operating flow rate of at least one second sparger 102. In some embodiments, the method may further include measuring 303 at least one parameter within the container 10, and changing 304 operating flow rate of at least one of at least one second sparger 102 according to changes in the at least one measured parameter.

In some embodiments, the first operating flow rate may be adapted to allow turbulent mixing the algae in the cultivation container, and the second operating flow rate may be adapted to allow assimilation of materials in a liquid in the cultivation container.

Unless explicitly stated, the method embodiments described herein are not constrained to a particular order in time or chronological sequence. Additionally, some of the described method elements can be skipped, or they can be repeated, during a sequence of operations of a method.

Various embodiments have been presented. Each of these embodiments may of course include features from other embodiments presented, and embodiments not specifically described may include various features described herein.

The invention claimed is:

1. An algae cultivation system, comprising:
   an algae cultivation container comprising algae in a cultivation medium;
   at least one light source configured to illuminate the interior of the container;
   at least one sensor, to measure at least one parameter within the container;
   at least one first source, said at least one first source including air and/or nitrogen gas;
   at least one second source, said at least one second source including gas with over 30% $CO_2$ concentration for biological consumption by the algae;
   at least one first sparger, to distribute a first fluid from the at least one first source into the container at a first operating flow rate;
   at least one second sparger, to distribute a second fluid from the at least one second source into the container at a second operating flow rate based on the at least one measured parameter;
   wherein the at least one first sparger has a nozzle diameter that is larger than 1 millimeter, and the at least one second sparger has a nozzle diameter that is smaller than 1 millimeter; and
   at least one controller configured to control the first operating flow rate, the second operating flow rate and the at least one light source,
   wherein the first fluid comprises air and/or nitrogen gas bubbles, the first operating flow rate is adapted to allow turbulent mixing of the algae and to yield illumination cycles for the algae in the cultivation container, and
   wherein the second fluid comprises gas bubbles with over 30% $CO_2$ concentration for biological consumption by the algae, and the second operating flow rate is adapted to allow assimilation of materials by the algae in the cultivation container from the second fluid; and
   wherein both fluids are introduced at a bottom of the cultivation container and rise through the cultivation medium to a top of the cultivation container.

2. The algae cultivation system of claim 1, further comprising a physical barrier that is set in the container to separate the first fluid distributed by the at least one first sparger from the second fluid distributed by the at least one second sparger.

3. The algae cultivation system of claim 1,
   wherein the first operating flow rate of the at least one first sparger is 100 millimeters/minute, and
   wherein the second operating flow rate of the at least one second sparger is 5 millimeters/minute.

4. The algae cultivation system of claim 1, wherein the controller is further configured to control the illumination wavelength of the at least one light source.

5. The algae cultivation system of claim 4, further comprising at least two light sources, wherein at least one light source is controlled to illuminate with a different intensity than another light source.

6. The algae cultivation system of claim 4, wherein the controller is further configured to control the at least one light source to illuminate with wavelength of 650 nanometers.

7. The algae cultivation system of claim 1, wherein the at least one controller is further configured to control an illumination photon flux density of the at least one light source to provide a daily amount of over 90% of maximal algae growth within the cultivation container.

8. The algae cultivation system of claim 7, wherein the controller is further configured to control the illumination wavelength of the at least one light source.

9. The algae cultivation system of claim 7, wherein the illumination photon flux density of the at least one light source is 1200 micromole/$m^2$/s.

10. The algae cultivation system of claim 7, wherein the at least one light source is a light emitting diode.

11. The algae cultivation system of claim 7, wherein at least a portion of the algae is *Isochrysis* galban.

12. The algae cultivation system of claim 7, comprising at least four light sources for each square meter.

13. The algae cultivation system of claim 7, wherein the controller is configured to control the at least one light source to illuminate with wavelength of 650 nanometers.

14. The algae cultivation system of claim 1, wherein both fluids are introduced at the bottom of the cultivation container at a same height.

* * * * *